US00PP36651P2

(12) United States Plant Patent
van Sambeek

(10) Patent No.: US PP36,651 P2
(45) Date of Patent: May 6, 2025

(54) ***ERYSIMUM* PLANT NAMED 'Doerywala'**

(50) Latin Name: *Erysimum hybrida*
Varietal Denomination: DOERYWALA

(71) Applicant: DUMMEN GROUP B.V., De Lier (NL)

(72) Inventor: Ellen van Sambeek, Oegstgeest (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 18/382,510

(22) Filed: Oct. 21, 2023

(51) Int. Cl.
*A01H 5/02* (2018.01)
*A01H 6/20* (2018.01)

(52) U.S. Cl.
USPC ..... Plt./263.1

(58) Field of Classification Search
USPC ..... Plt./263.1
See application file for complete search history.

*Primary Examiner* — Shubo (Joe) Zhou
*Assistant Examiner* — Zachariah Allan Kay
(74) *Attorney, Agent, or Firm* — C. Anne Whealy

(57) ABSTRACT

A new and distinct cultivar of *Erysimum* plant named 'Doerywala', characterized by its upright and mounding plant habit; freely branching habit; dense and bushy habit; freely and continuous flowering habit; long flowering period; and large light purple-colored flowers.

2 Drawing Sheets

Figure 1:
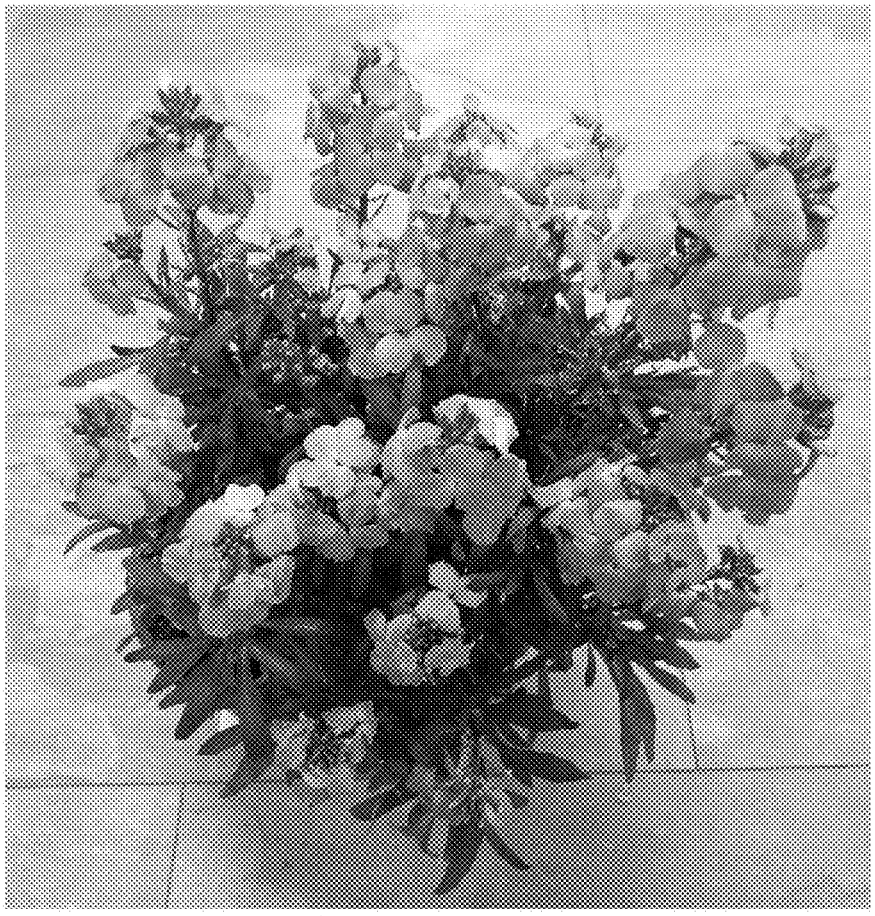

Botanical designation: *Erysimum hybrida.*
Cultivar denomination: 'DOERYWALA'.

STATEMENT REGARDING PRIOR DISCLOSURES BY INVENTOR & APPLICANT/ASSIGNEE

A European Community Plant Breeder's Rights application for the instant plant was filed by the Applicant/Assignee, Dümmen Group B.V. of De Lier, The Netherlands on Jul. 25, 2023, application number 2023/1569. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Erysimum* plant, botanically known as *Erysimum hybrida*, commonly referred to as Wallflower and hereinafter referred to by the name 'Doerywala'.

The new *Erysimum* plant is a product of a planned breeding program conducted by the Inventor in Aalsmeer, The Netherlands. The objective of the breeding program was to develop new *Erysimum* plants with numerous large and attractive flowers.

The new *Erysimum* plant originated from a cross-pollination in March 2018 in Aalsmeer, The Netherlands of a proprietary selection of *Erysimum hybrida* identified as code number ER16-000007-002, not patented, as the female, or seed, parent, with a proprietary selection of *Erysimum hybrida* identified as code number ER16-000009-002, not patented, as the male, or pollen, parent. The new *Erysimum* plant was discovered and selected by the Inventor as a single flowering plant within the progeny of the stated cross-pollination in a controlled greenhouse environment in Aalsmeer, The Netherlands in March 2019.

Asexual reproduction of the new *Erysimum* plant by vegetative terminal cuttings in a controlled greenhouse environment in Aalsmeer, The Netherlands since March 2019 has shown that the unique features of this new *Erysimum* plant are stable and reproduced true to type in successive generations.

SUMMARY OF THE INVENTION

Plants of the new *Erysimum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doerywala'. These characteristics in combination distinguish 'Doerywala' as a new and distinct *Erysimum* plant:

1. Upright and mounding plant habit.
2. Freely branching habit; dense and bushy habit.
3. Freely and continuous flowering habit.
4. Long flowering period.
5. Large light purple-colored flowers.
6. Tolerant to low and high temperatures.

Plants of the new *Erysimum* differ primarily from plants of the female parent selection in flower color as flowers of plants of the new *Erysimum* are lighter purple in color than flowers of plants of the female parent selection.

Plants of the new *Erysimum* differ primarily from plants of the male parent selection in flower color as flowers of plants of the new *Erysimum* are light purple in color whereas flowers of plants of the male parent selection are red in color.

Plants of the new *Erysimum* can also be compared to *Erysimum hybrida* 'Poem Pastel', not patented. In side-by-side comparisons, plants of the new *Erysimum* differ from plants of 'Poem Pastel' in the following characteristics:

1. Plants of the new *Erysimum* are more compact than plants of 'Poem Pastel'.
2. Plants of the new *Erysimum* have larger flowers than plants of 'Poem Pastel'.
3. Flowers of plants of the new *Erysimum* are light purple in color whereas flowers of plants of 'Poem Pastel' are pastel pink and yellow in color.

BRIEF DESCRIPTION OF THE PHOTOGRAPHS

The accompanying colored photographs illustrate the overall appearance of the new *Erysimum* plant showing the colors as true as it is reasonably possible to obtain in colored reproductions of this type. Colors in the photographs may differ slightly from the color values cited in the detailed botanical description which accurately describe the colors of the new *Erysimum* plant.

The photograph on the first sheet (FIG. 1) is a side perspective view of a typical flowering plant of 'Doerywala' grown in a container.

Figure 2:
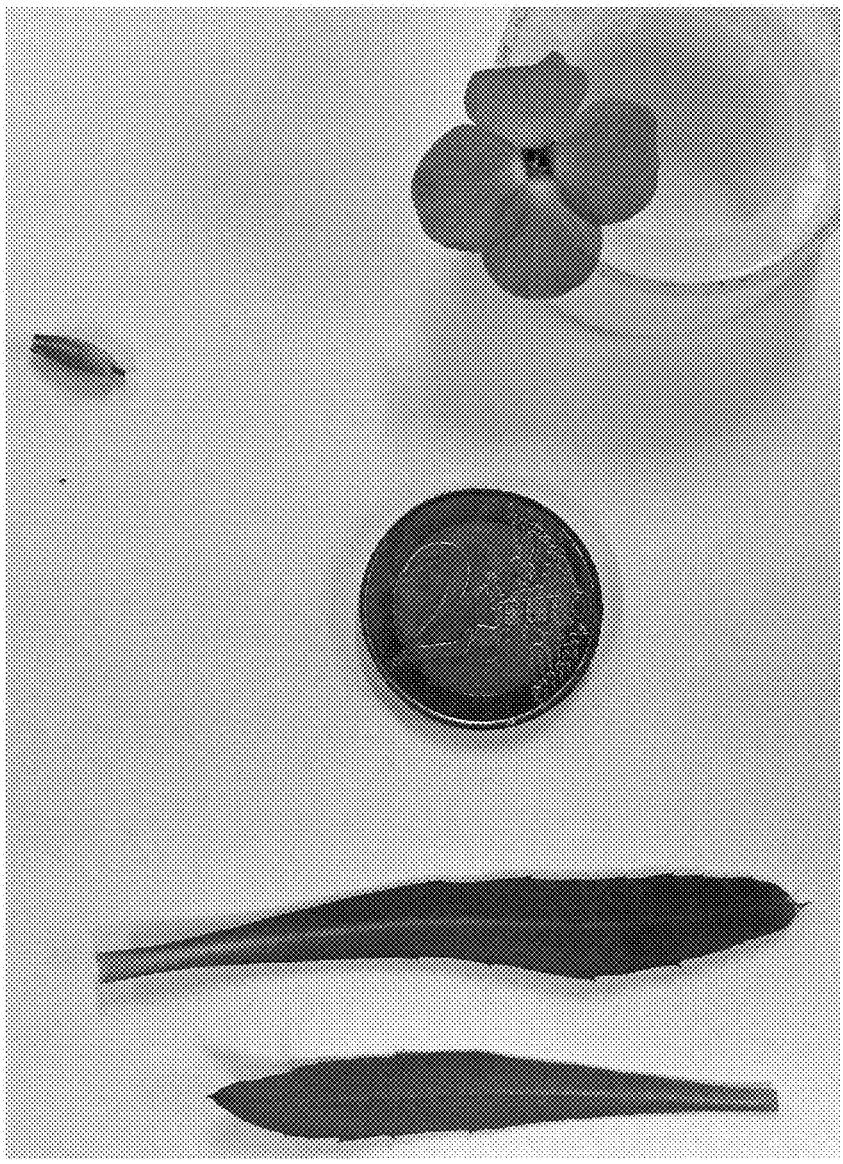

The photograph on the second sheet (FIG. 2) is a close-up view of a typical flower bud, the upper surface of a typical flower and the upper and lower surfaces of typical leaves.

DETAILED BOTANICAL DESCRIPTION

The aforementioned photographs and following observations and measurements describe plants grown during the early spring in 17-cm containers in a glass-covered greenhouse in Aalsmeer, The Netherlands and under cultural practices typical of commercial *Erysimum* production. During the production of the plants, average daily temperatures were 21 C and average night temperatures were 15 C. Plants were 25 weeks old when the photographs and description were taken. In the following description, color references are made to The Royal Horticultural Society Colour Chart, Second Edition, except where general terms of ordinary dictionary significance are used.

Botanical classification: *Erysimum hybrida* 'Doerywala'.

Parentage:

*Female, or seed, parent*.—Proprietary selection of *Erysimum hybrida* identified as code number ER16-000007-002, not patented.

*Male, or pollen, parent*.—Proprietary selection of *Erysimum hybrida* identified as code number ER16-000009-002, not patented.

Propagation:

*Type*.—Terminal vegetative cuttings.

*Time to initiate roots, summer*.—About twelve days at temperatures about 26 C.

*Time to initiate roots, winter*.—About 16 days at temperatures about 23 C.

*Time to produce a rooted young plant, summer*.—About 16 days at temperatures about 23 C.

*Time to produce a rooted young plant, winter*.—About 20 days at temperatures about 18 C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Perennial garden or container plant; upright to mounding plant habit; freely branching habit with about 30 lateral branches developing per plant; dense and bushy appearance.

*Plant height*.—About 36 cm.

*Plant diameter* (*area of spread*).—About 27 cm.

*Lateral branches*.—Length: About 23 cm. Diameter: About 3 mm. Internode length: About 4 mm. Strength: Moderately strong. Aspect: About 25 to 45 degrees from vertical. Texture and luster: Slightly pubescent; glossy. Color, developing: Close to 144C. Color, developed: Close to 144A.

Leaf description:

*Arrangement*.—Alternate; simple; sessile.

*Length*.—About 6.5 cm.

*Width*.—About 1 cm.

*Shape*.—Oblanceolate.

*Apex*.—Acute.

*Base*.—Cuneate.

*Margin*.—Entire with a few indentations.

*Texture and luster, upper and lower surfaces*.—Smooth, glabrous; semi-glossy.

*Venation pattern*.—Single midvein discernible.

*Color*.—Developing leaves, upper and lower surfaces: Close to 137C. Fully developed leaves, upper surface: Close to 137A; venation, close to 138B. Fully developed leaves, lower surface: Close to 137C; venation, close to 138B.

Flower description:

*Flower type and habit*.—Large rounded cruciform flowers arranged in dense racemes; flowers face mostly upright to outwardly; freely flowering habit, about twelve flowers per inflorescence and about 630 flowers developing per plant during the flowering season.

*Natural flowering season*.—Plants of the new *Erysimum* begin flowering about 22 weeks after planting; relatively long flowering period, plants flower continuously from spring until autumn in The Netherlands; flowers not persistent.

*Fragrance*.—Moderately fragrant; sweet.

*Inflorescence height*.—About 6 cm.

*Inflorescence diameter*.—About 4.5 cm.

*Flower diameter*.—About 2.2 cm.

*Flower depth* (*height*).—About 1 cm.

*Flower buds*.—Length: About 1.1 cm. Diameter: About 4 mm. Shape: Elliptic. Texture and luster: Smooth, glabrous; matte. Color: Close to 157C slightly tinged with close to 84C.

*Petals*.—Quantity and arrangement: Three to four petals arranged in a single whorl. Length: About 1.1 cm. Width: About 1.1 cm. Shape: Obovate. Apex: Obtuse with truncate tendencies. Base: Cuneate. Margin: Entire; slightly undulate. Texture and luster, upper and lower surfaces: Smooth, glabrous; matte. Color: When opening, upper and lower surfaces: Close to 84B. Fully opened, upper and lower surfaces: Close to 84A; venation, close to 84A; color does not change with subsequent development.

*Sepals*.—Quantity and arrangement: Four sepals arranged in a single whorl; calyx, tubular. Calyx length: About 1 cm. Calyx diameter: About 5 mm. Length: About 1 cm. Width: About 2 mm. Shape: Subulate. Apex: Acuminate. Base: Cuneate. Margin: Entire. Texture and luster, upper and lower surfaces: Smooth, glabrous; semi-glossy. Color, upper and lower surfaces: Close to 144A.

*Pedicels*.—Length: About 4 mm. Width: About 1 mm. Strength: Flexible. Aspect: About 45 to 80 degrees from vertical. Texture and luster: Smooth, glabrous; semi-glossy. Color: Close to 143A.

*Reproductive organs*.—Stamens: Quantity per flower: Six. Filament length: About 3 mm. Filament color: Close to 145C. Anther shape: Deltoid. Anther size: About 1 mm by 3 mm. Anther color: Close to 160B. Pollen amount: Sparse. Pollen color: Close to 158A. Pistils: Quantity per flower: One. Pistil length: About 1.1 cm. Style length: About 1 mm. Style color: Close to 144A. Stigma diameter: About 1 mm. Stigma shape: Rounded, capitate. Stigma color: Close to 144A. Ovary color: Close to 155D.

*Seeds/fruits*.—To date, seed and fruit development has not been observed on plants of the new *Erysimum*.

Pathogen & pest resistance: To date, plants of the new *Erysimum* have not been noted to be resistant to pathogens or pests common to *Erysimum* plants.

Garden performance: Plants of the new *Erysimum* have been observed to tolerate temperatures ranging from about −20° C. to about 35° C. and are suitable for U.S.D.A. Hardiness Zone 6.

It is claimed:

1. A new and distinct *Erysimum* plant named 'Doerywala' as herein illustrated and described.

* * * * *